(12) United States Patent
Allen, IV et al.

(10) Patent No.: US 11,730,941 B2
(45) Date of Patent: Aug. 22, 2023

(54) SURGICAL TOOL POSITIONING DEVICE

(71) Applicant: Covidien LP, Mansfield, MA (US)

(72) Inventors: James D. Allen, IV, Broomfield, CO (US); Jing Zhao, Superior, CO (US)

(73) Assignee: Covidien LP, Mansfield, MA (US)

( * ) Notice: Subject to any disclaimer, the term of this patent is extended or adjusted under 35 U.S.C. 154(b) by 643 days.

(21) Appl. No.: 16/806,806

(22) Filed: Mar. 2, 2020

(65) Prior Publication Data

US 2020/0297988 A1   Sep. 24, 2020

Related U.S. Application Data

(60) Provisional application No. 62/819,699, filed on Mar. 18, 2019.

(51) Int. Cl.

| | |
|---|---|
| *A61M 39/02* | (2006.01) |
| *A61B 17/34* | (2006.01) |
| *A61B 1/00* | (2006.01) |
| *A61B 17/00* | (2006.01) |
| *A61B 90/10* | (2016.01) |

(52) U.S. Cl.
CPC ..... *A61M 39/0247* (2013.01); *A61B 1/00154* (2013.01); *A61B 17/3423* (2013.01); *A61B 17/3462* (2013.01); *A61B 2017/00535* (2013.01); *A61B 2090/103* (2016.02); *A61M 2039/0279* (2013.01); *A61M 2039/0297* (2013.01)

(58) Field of Classification Search
CPC ...... A61M 39/0247; A61M 2039/0279; A61M 2039/0297; A61M 25/0119; A61B 1/00154; A61B 17/3423; A61B 17/3462; A61B 2017/00535; A61B 2090/103; A61B 1/00151; A61B 2017/3435
See application file for complete search history.

(56) References Cited

U.S. PATENT DOCUMENTS

| | | | | |
|---|---|---|---|---|
| 3,168,092 | A * | 2/1965 | Silverman | A61B 46/13 600/7 |
| 3,757,788 | A * | 9/1973 | Renfroe | A61B 17/22 604/27 |
| 5,259,364 | A * | 11/1993 | Bob | A61B 1/31 600/129 |
| 6,077,219 | A * | 6/2000 | Viebach | A61B 1/2736 600/114 |
| 6,554,793 | B1 * | 4/2003 | Pauker | A61B 1/00151 604/95.01 |
| 2017/0265724 | A1 * | 9/2017 | Lichtenstein | A61B 1/00151 |

* cited by examiner

*Primary Examiner* — Theodore J Stigell
(74) *Attorney, Agent, or Firm* — Carter, DeLuca & Farrell LLP (57) ABSTRACT

A positioning device is provided for delivering or guiding a surgical device into a lumen of a body vessel to a position adjacent target tissue. The device includes a housing, an elongate sleeve, and a source of pressurized fluid. The sleeve has a first end coupled to a delivery side of the housing, a second end positioned on a return side of the housing, and an inverted distal portion positioned between the first and second ends. One second end of the sleeve can be furled about a support member supported on the housing. A distal portion of the sleeve defines a cavity that communicates with a pressure chamber within the housing. When pressurized fluid is directed into the pressure chamber, the pressurized fluid flows into the cavity of the distal portion of the sleeve to advance the sleeve away from the housing.

16 Claims, 11 Drawing Sheets

SURGICAL TOOL POSITIONING DEVICE

CROSS-REFERENCE TO RELATED APPLICATION

This application claims the benefit of and priority to U.S. Provisional Patent Application No. 62/819,699 filed Mar. 18, 2019, the entire disclosure of which is incorporated by reference herein.

BACKGROUND

1. Technical Description

The disclosure is directed to a device and method for positioning a surgical tool within a body lumen and, more particularly, to a device and method for positioning an endoscope within a body lumen.

2. Background of Related Art

Endoscopes are routinely inserted into body vessels to allow a surgeon to visualize the interior of the body vessel for diagnostic purposes and/or to treat tissue. In some surgical procedures, it is necessary to access a body vessel through a natural body orifice. These procedures, also known as natural orifice transluminal endoscopic surgeries, sometimes require advancement of an endoscope deep into the body vessel. In these procedures, advancement may be impeded by the curvature of the body vessel.

A continuing need exists in the art for an endoscope positioning device that is capable of allowing an endoscope to traverse deep into a lumen defined by the body vessel without damaging the body vessel.

SUMMARY

One aspect of the disclosure is directed to a positioning device for accessing target tissue within a body lumen with a surgical device. The positioning device includes a housing, a sleeve, and a source of pressurized fluid. The housing defines a central bore and a pressure chamber and includes a delivery side and a return side. The sleeve has a first end and a second end and an inverted distal portion located between the first and second ends. The first end of the sleeve is supported on the delivery side of the housing and the second end of the sleeve supported on the return side of the housing. The inverted distal portion defines a cavity and a central guide channel. The cavity is in communication with the pressure chamber of the housing. The source of pressurized fluid communicates with the pressure chamber of the housing, wherein when pressurized fluid is directed into the pressure chamber, the pressurized fluid enters the cavity of the inverted distal portion of the sleeve to advance the inverted distal portion of the sleeve away from the housing.

In embodiments, an annular support mechanism is supported on the housing and the sleeve is wound about the annular support mechanism.

In some embodiments, the annular support mechanism is supported on the delivery side of the housing.

In certain embodiments, the annular support mechanism is supported on the return side of the housing.

In embodiments, the annular support mechanism includes a motor driven toroid.

In embodiments, the annular support mechanism includes a rotatable toroid.

In some embodiments, a first clamp is supported on the housing adjacent the annular support mechanism, the first clamp movable from an unclamped position to a clamped position to control an advancement rate of the distal inverted portion of the sleeve.

In certain embodiments, a first actuator is coupled to the first clamp, and the first actuator is actuatable to selectively move the first clamp between an unclamped position and a clamped position.

In embodiments, a first flexible sealing member is positioned about the central bore of the housing to engage the sleeve and prevent fluid from passing between the flexible sealing member and the sleeve.

In embodiments, a second flexible sealing member is positioned on the housing to engage an inner surface of an outer portion of the sleeve to prevent fluid from passing between the sleeve and the housing.

In some embodiments, the flexible sealing member has a tear-drop shaped cross-section.

In certain embodiments, the flexible sealing member includes a duck-bill valve.

In certain embodiments, a fluid control valve includes an inlet that communicates with the source of pressurized fluid and an outlet that communicates with the pressure chamber in the housing.

In embodiments, the inlet to the fluid control valve also communicates with a vent.

In some embodiments, a surgical device has a flange and is supported within the guide channel, wherein the flange is positioned distal of the inverted distal portion of the sleeve such that advancement of the sleeve away from the housing moves the surgical device away from the housing.

In certain embodiments, the guide channel on the return side of the housing is open to receive a surgical device.

In embodiments, the sleeve is formed of an aromatic polyamide such as Kevlar®. Alternately, other materials of construction are envisioned including cloth, nylon, polyester, polyethylene, woven fabrics, composites, or the like.

Another aspect of the disclosure is directed to a delivery device for positioning a surgical device adjacent target tissue within a body lumen. The delivery device includes a housing, a sleeve, a source of pressurized fluid, and a surgical device. The housing defines a central bore and a pressure chamber that communicates with the central bore, and includes a delivery side and a return side. The sleeve has a first end and a second end and an inverted distal portion located between the first and second ends. The first end of the sleeve is supported on the delivery side of the housing and second end of the sleeve is supported on the return side of the housing. The inverted distal portion defines a cavity and a central guide channel. The cavity is in communication with the pressure chamber. The source of pressurized fluid communicates with the pressure chamber of the housing. The surgical device extends through the guide channel and includes a body having a flange that is positioned distally of the inverted distal portion of the sleeve. When pressurized fluid is directed to the pressure chamber, the pressurized fluid is directed into the cavity of the inverted distal portion of the sleeve to advance the inverted distal portion of the sleeve and the surgical device away from the housing.

In embodiments, the surgical device is an endoscope.

In some embodiments, the delivery device includes an annular support mechanism and a first clamp. The annular support mechanism includes a rotatable toroid supported on the housing. The sleeve is wound about rotatable toroid. The first clamp is supported on the housing adjacent the annular support mechanism and is movable from an unclamped position to a clamped position to control an advancement rate of the distal inverted portion of the sleeve.

Another aspect of the disclosure is directed to a method of positioning a surgical device adjacent target tissue within a lumen of a body vessel. The method includes securing a first end of a tubular sleeve to a delivery side of a housing; inverting the sleeve within the housing and positioning a second end of the sleeve on a return side of the housing such that the sleeve defines a central guide channel and the inverted distal portion of the sleeve defines a cavity; and coupling the cavity defined by the inverted distal portion of the sleeve with a pressure chamber in the housing to facilitate advancement of the inverted distal portion of the sleeve away from the housing through a lumen of a body vessel.

In embodiments, the method includes controlling the advancement rate of the inverted distal portion of the sleeve.

In some embodiments, controlling the advancement rate of the inverted distal portion of the sleeve includes actuating a first clamp to clamp and unclamp the sleeve.

In certain embodiments, delivering pressurized fluid to the cavity includes advancing the distal inverted portion of the sleeve within the lumen of the body vessel to a point midway between the housing and the target tissue.

In embodiments, the method further includes positioning a surgical device within the guide channel such that the surgical device is frictionally retained within the guide channel, and advancing the distal inverted portion to the target tissue with the surgical device supported on the sleeve.

BRIEF DESCRIPTION OF THE DRAWINGS

Various embodiments of the disclosed positioning device for a surgical device are described herein below with reference to the drawings, wherein.

DETAILED DESCRIPTION OF EMBODIMENTS

The disclosed positioning device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 1:
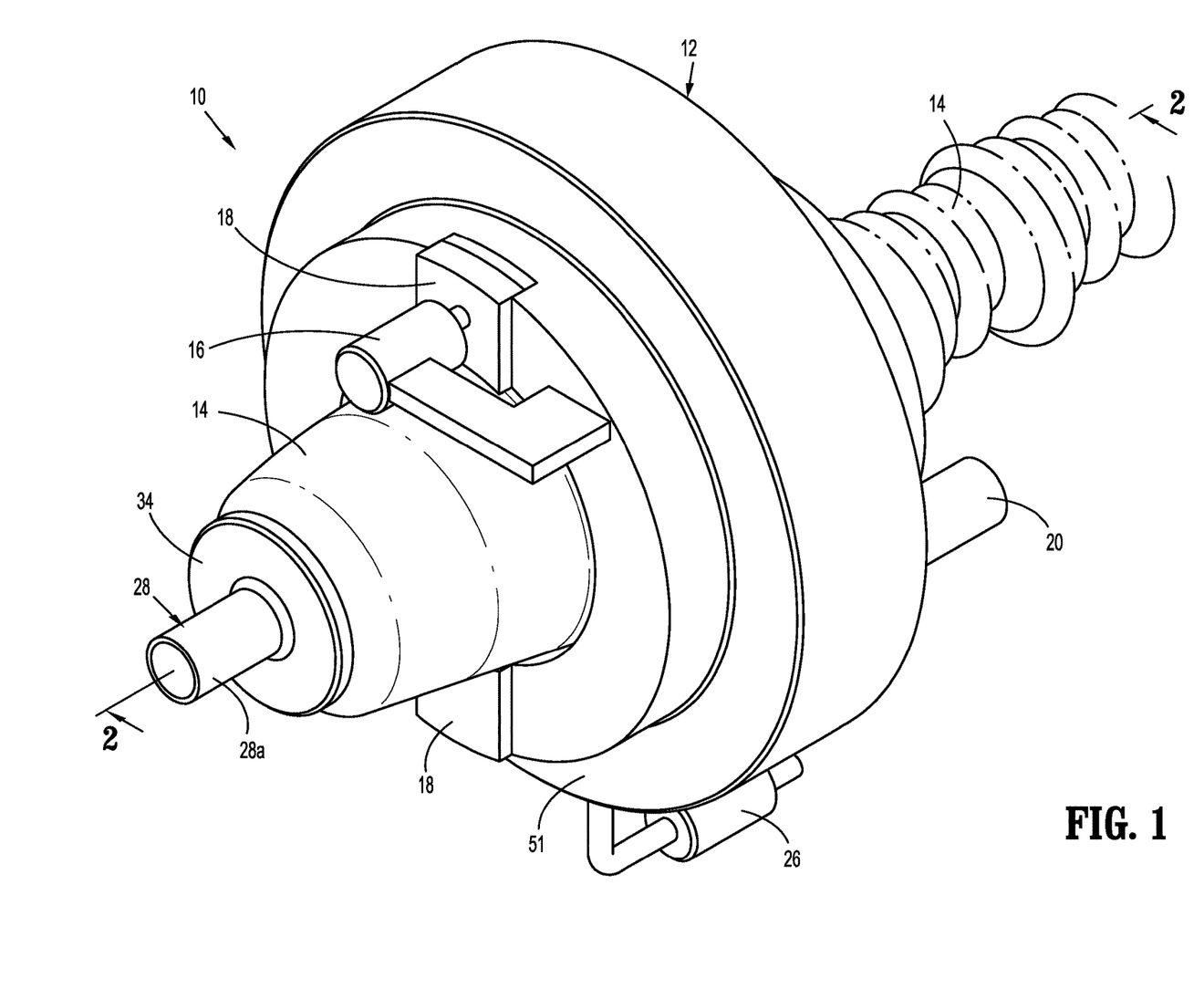
FIG. 1 is a side perspective view of an exemplary embodiment of the disclosed surgical device positioning device supporting an endoscope with an elongate sleeve of the positioning device extending from a return side of a housing of the device.
Figure 2:
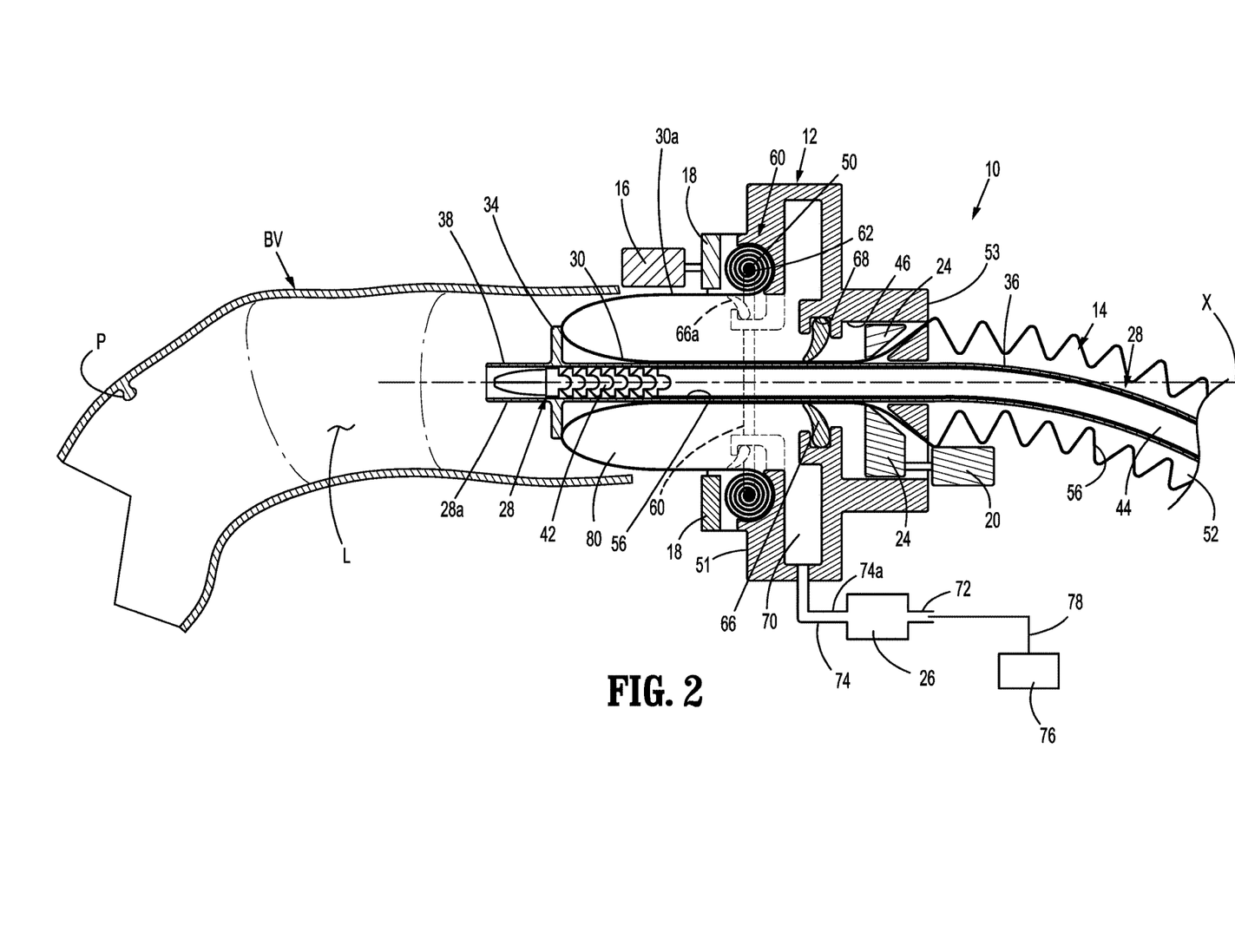
FIG. 2 is a side cross-sectional view of the endoscope positioning device shown in FIG. 1 with the endoscope positioned within an entry opening of a natural body orifice and the sleeve of the positioning device in a retracted position within a body lumen.
Figure 2A:
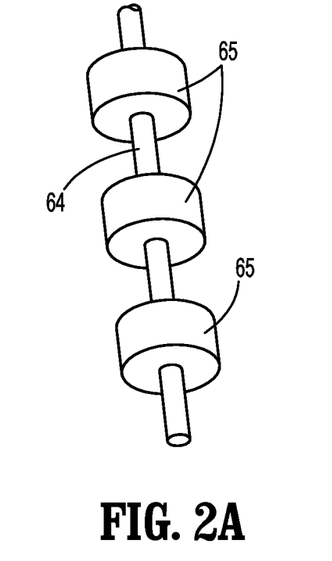
FIG. 2A is a side perspective view of a portion of a drive member of a winding mechanism of the positioning device shown in FIG. 1.
Figure 2B:
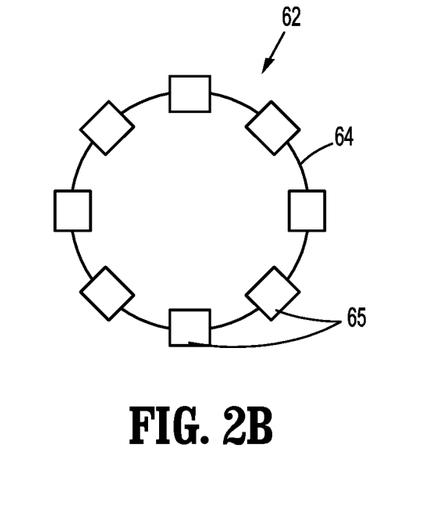
FIG. 2B is a side perspective view of the drive member of the winding mechanism of the positioning device shown in FIG. 1.

Referring to FIGS. 1 and 2, the disclosed positioning device is shown generally as positioning device 10 and includes a housing 12, an elongated tubular sleeve 14, a first actuator 16, first clamps 18, a second actuator 20, second clamps 24 (FIG. 2), and a fluid control valve 26. A surgical device, e.g., an endoscope 28, is supported on a distal portion 30 (FIG. 2) of the sleeve 14 and is movable with the sleeve 14 within a lumen "L" defined by a body vessel "By" (FIG. 2) as described in detail below.

FIG. 2 illustrates the surgical device, e.g., the endoscope 28, supported on a distal inverted portion 30 of the elongate sleeve 14 as the endoscope 28 and the sleeve 14 are introduced through a natural body orifice into the lumen "L" of the body vessel "By". The endoscope 28 is positioned within the sleeve 14 and includes a body 28a and an annular support flange 34 that extends transversely from the body 28a to a position distally of the distal portion 30 of the sleeve 14. When the sleeve 14 is advanced from the housing 12, the support flange 34 is positioned to be engaged by the distal inverted portion 30 of the sleeve 14 to advance the endoscope 28 within the lumen "L".

In embodiments, the endoscope 28 includes an elongate flexible body 36 and a visualization device 38 that is supported on a distal portion of the flexible body 36. The flexible body 36 may define one or more channels 44 for receiving a surgical device such as a dissector, a grasper, a biopsy device, for treating tissue or the like. For example, a surgical device may be extendable through the endoscope 28 to remove polyps "P" (FIG. 2) from within the body vessel "By" during a colonoscopy procedure. In some embodiments, the distal portion of the flexible body 36 of the endoscope 28 may include a series of interconnected links 42 that are pivotally coupled together, e.g., via universal joints, to control positioning of the distal portion of the endoscope 28 within the body vessel "By".

The housing 12 of the positioning device 10 defines a longitudinal axis "X" and a central bore 46 that is coaxial with longitudinal axis "X". The housing 12 includes a delivery side 51 from which the distal inverted portion 30 extends, and a return side 53 from which the second end of the sleeve 14 extends. The first and second actuators 16 and 20 are supported on the housing 12 and are coupled to the first clamps 18 and the second clamps 24, respectively. The first actuator 16 is operable to move the first clamps 18 from a first unclamped position (FIG. 3) to a second clamped position (FIG. 4). Similarly, the second actuator 20 is operable to move the second clamps 24 from a first unclamped position (FIG. 3) to a second clamped position (FIG. 5). The first and second actuators 16 and 20 can be actuated independently of each other to control delivery and winding of the elongate sleeve 14 as described below.

The sleeve 14 extends through the central bore 46 of the housing 12 and has a first end 50 that is mounted to the delivery side 51 of the housing 12. The sleeve 14 is inverted such that the second end 52 of the sleeve 14 extends through the central bore 46 of the housing 12 from the return side 53 of the housing 12. The inverted distal portion 30 of the sleeve 14 defines a central channel 56 that extends between the first and second ends 50 and 52 of the sleeve 14. The second end of the sleeve 14 is open to allow the surgical device, e.g., the endoscope 28, to be fed into the central bore 56.

Figure 2C:
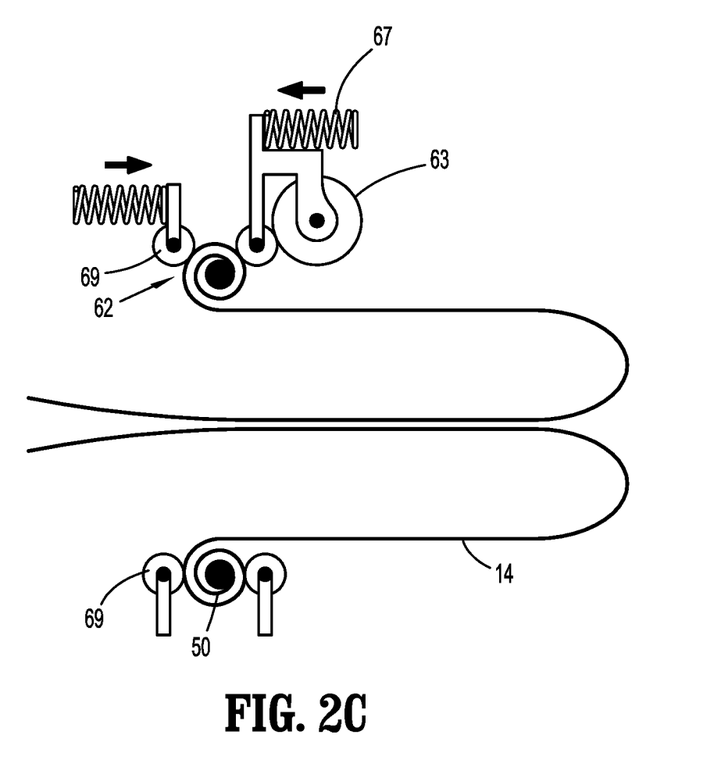
FIG. 2C is a side view of a braking device of the positioning device shown in FIG. 1 engaged with the sleeve with the sleeve supported on the drive member.

In embodiments, the delivery side of the housing 12 includes an annular sleeve support mechanism 60 for supporting and rolling the sleeve 14. FIGS. 2-2C illustrate the annular sleeve support mechanism 60 which includes toroid 62 including a flexible annular support ring 64 and one or more rollers 65 supported on the ring 64 for rotation. The first end 50 (FIG. 2C) of the sleeve 14 is wound about the toroid 62 in a manner to allow the sleeve 14 to be selectively rolled about the toroid 62 or dispensed from the toroid 62 to deliver the sleeve 14 into the body vessel "By" (FIG. 2) or to withdraw the sleeve 14 from within the body vessel "By".

In embodiments, an electric motor driven wheel 63 (FIG. 2C) or the like is positioned adjacent to the toroid 62 to engage the sleeve 14. The electric motor driven wheel 63 is operable to wind or unwind the sleeve 14 about the toroid 62. A biasing member 67 (FIG. 2C) may be provided to urge the wheel 63 into engagement with the sleeve 14. Non-driven guide wheels 69 may also be provided to ensure that the sleeve 14 remains in tension as the sleeve 14 is wound about the toroid 62.

It is contemplated that a variety of different types of drive members can be used to wind the sleeve 14 about the toroid 62. For example, an electric motor can be coupled directly to the ring 64 to rotate the ring 64 to wind and unwind the sleeve 14 about the toroid 62.

Figure 3:
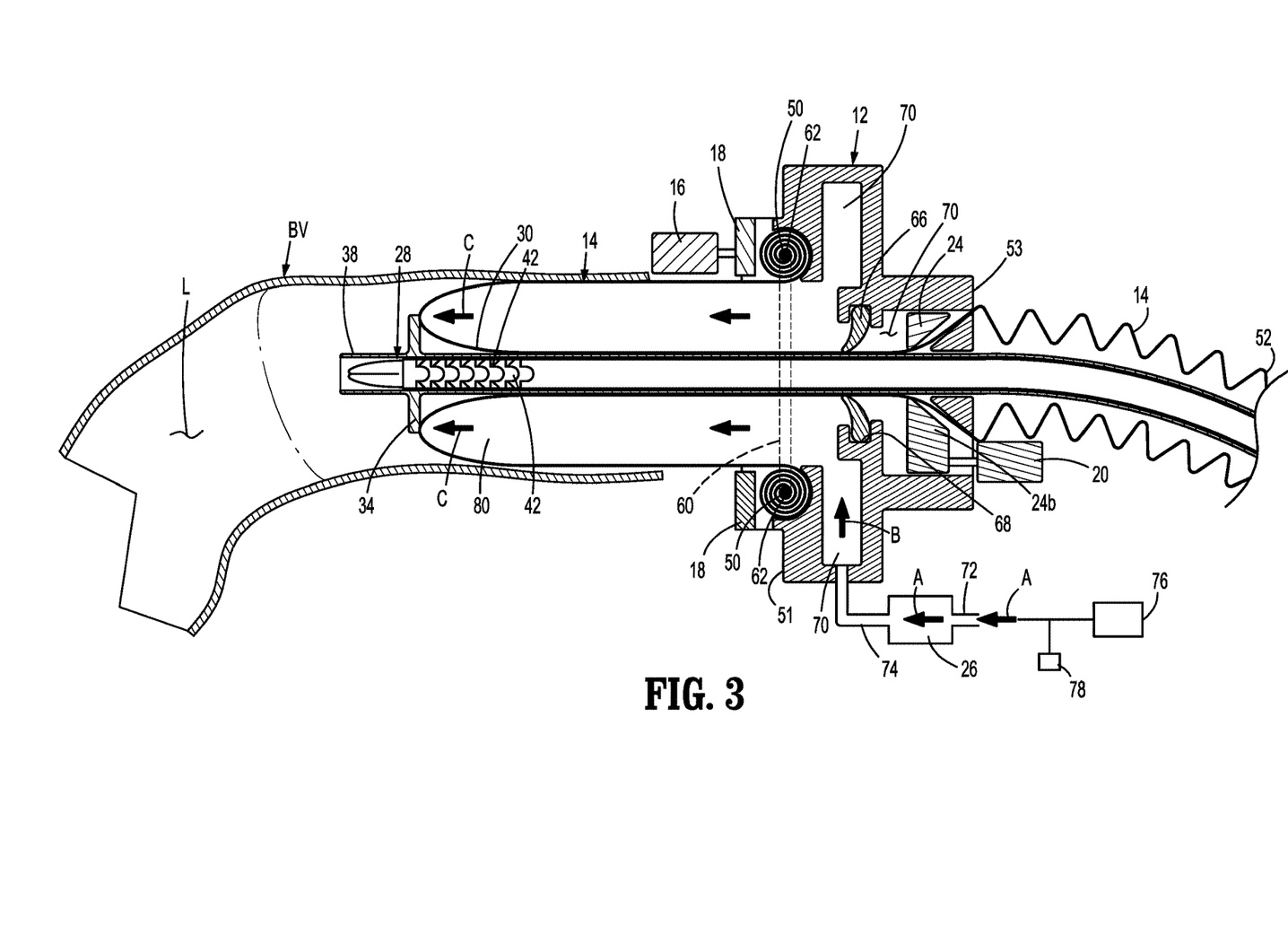
FIG. 3 is a side cross-sectional view of the positioning device shown in FIG. 2 with the sleeve extending through the natural body orifice to a position within the body vessel with the endoscope supported on the sleeve.
Figure 4:
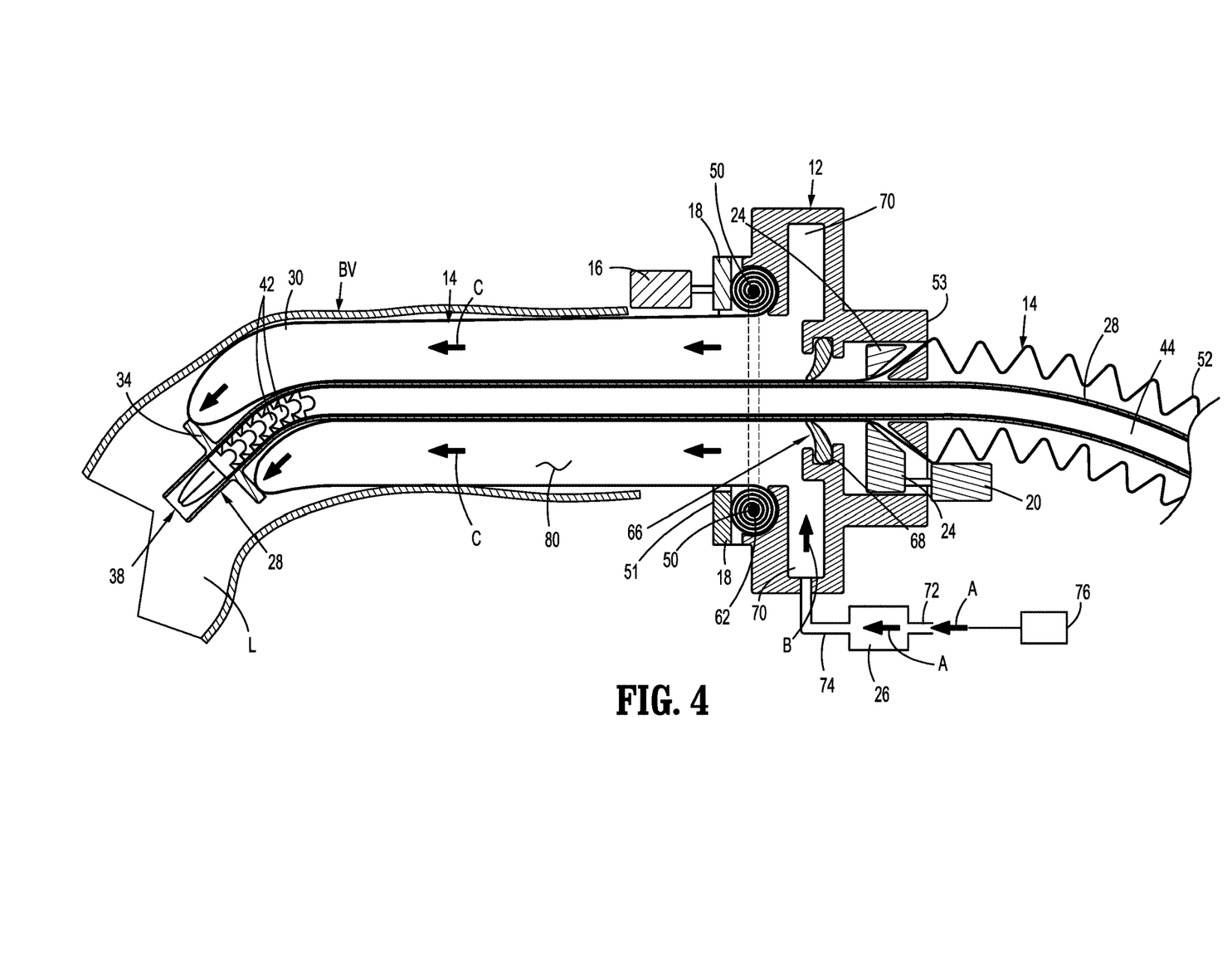
FIG. 4 is a side cross-sectional view of the positioning device shown in FIG. 3 with the sleeve and the endoscope advanced further into the body vessel.
Figure 5:
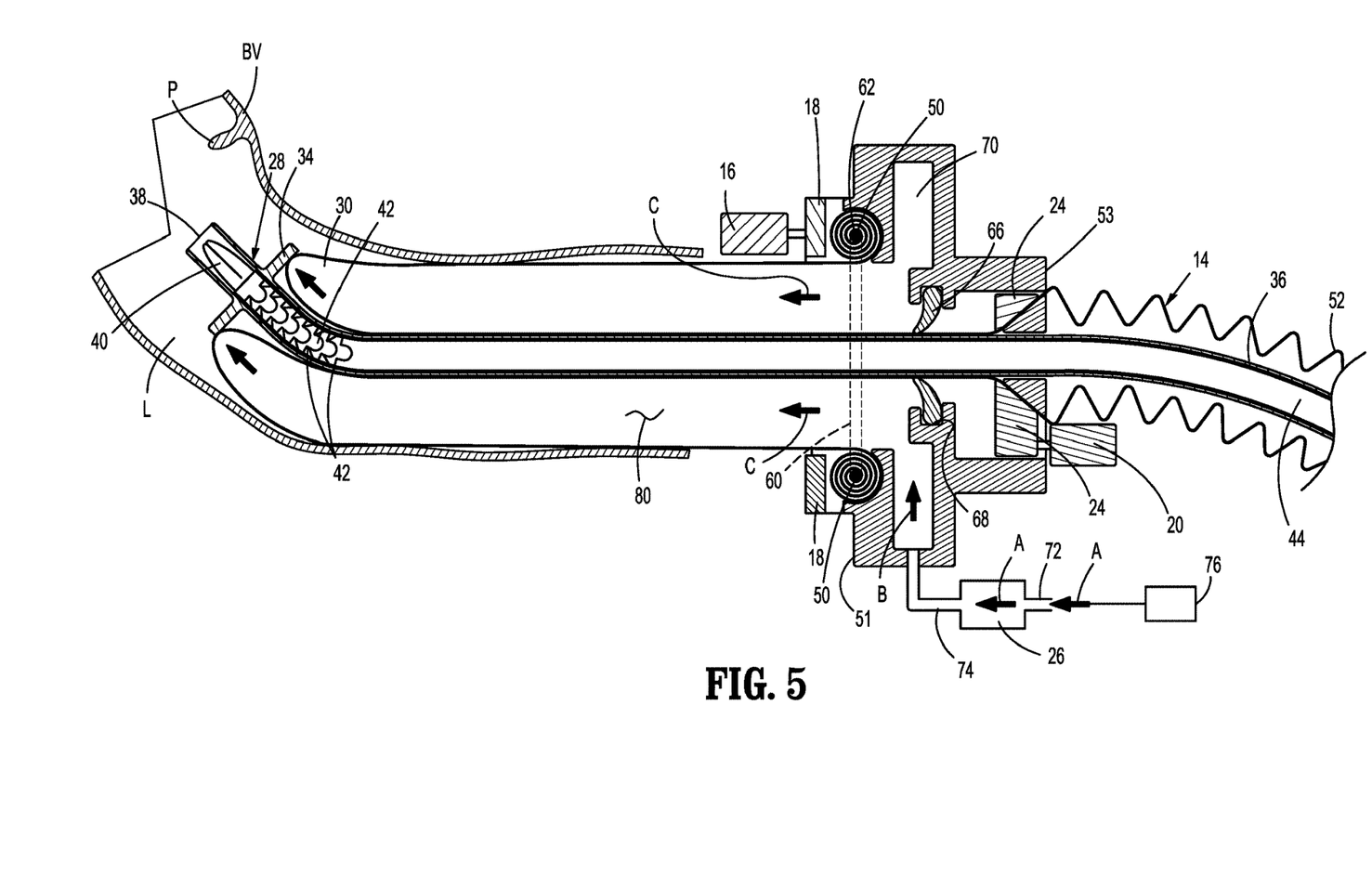
FIG. 5 is a side cross-sectional view of the positioning device shown in FIG. 2 with the endoscope advanced further into the body vessel.

FIGS. 3-5 illustrate the delivery device 10 as the sleeve 14 is advanced through the lumen "L" of the body vessel "By". The delivery device 10 includes an annular, flexible sealing member 66 to provide a seal about the inverted portion 30 of the sleeve 14 and the endoscope 28. In embodiments, the sealing member 66 is supported within an annular recess 68 defined within the housing 12 of the positioning device 10 and has a tear-drop shaped cross-sectional configuration. Alternately, other sealing member configurations are envisioned. For example, the sealing member 66 may also be in the form of a duck-bill valve 66' (FIG. 6B) which is discussed in further detail below. The sealing member 66 is formed of a flexible material, e.g., rubber, and is positioned to engage an outer surface of the sleeve 14 to prevent fluid, e.g., air, from passing between the sleeve 14 and the housing 12 through the proximal end of the central opening 46.

In some embodiments, an additional sealing member 66a is provided to engage an internal surface of an outer portion 30a (FIG. 2 in phantom) of the sleeve 14 to provide a seal between the inner surface of the sleeve 14 and the housing 12 of the positioning device 12 adjacent the sleeve support mechanism 60.

The housing 12 defines a pressure chamber 70 that communicates with the fluid control valve 26 via a conduit 74. The fluid control valve 26 has an inlet 72 that communicates with a source of pressurized fluid 76 and an outlet 74a (FIG. 2) that communicates with the conduit 74. In some embodiments, the inlet 72 can also communicate with a vent 78 that can vent the pressure chamber 70 if necessary.

As described above, the sleeve 14 is tubular and has its first end 50 wound about the toroid 62 and a second end 52 that extends through the central bore 46 and to the return side of the housing 12. The distal inverted portion 30 of the sleeve 14 defines an enclosed cavity 80 with the flexible sealing member 66 that communicates with the pressure chamber 70 of the housing 12. When the fluid control valve 26 is actuated to pressurize the chamber 70 in the housing 12, the cavity 80 defined by the sleeve 14 is pressurized such that a force is applied to the distal inverted portion 30 of the sleeve 14. This force on the inverted distal portion 30 of the sleeve 14 urges the sleeve 14 to unfurl from about the toroid 62 and extend outwardly of the housing 12 into the lumen "L" of the body cavity "By". The first and second clamps 18, and 24 are moved between clamped and unclamped positions to control delivery (or withdrawal of) the sleeve 14.

As discussed above, the housing 12 supports the first actuator 16 and the first clamps 18 on the delivery side 51 of the housing 12. The first actuator 16 is coupled to the first clamps 18 such that the first clamps 18 can be selectively moved from an unclamped position (FIG. 3) spaced from the sleeve 14 on the toroid 62 to allow unfurling of the sleeve 14 from the toroid 62 to a clamped position (FIG. 4) engaged with a portion of the sleeve 14 that is wound about the toroid 62 to prevent unfurling of the sleeve 14 from the toroid 62.

The housing 12 also supports the second actuator 20 and the second clamp 24 on the return side of the housing 12. The second actuator 20 is coupled to the second clamps 24 such that the second clamps 24 can be selectively moved from an unclamped position (FIG. 3) spaced from the sleeve 14 to allow the sleeve 14 to move through the central opening 46 of the housing 12 from the return side 53 of the housing 12 to the delivery side 51 of the housing 12 to a clamped position engaged with the sleeve 14 to prevent the sleeve 14 being fed through the housing 12. In embodiments, the first clamps 18 are spaced about the delivery side 51 of the housing 12 adjacent to the toroid 62 and the second clamp 24 includes one or more clamping members 24 spaced about the central opening 46 adjacent the return side of the housing 12.

In use, the distal inverted portion 30 of the sleeve 14 is positioned within the lumen "L" of a body vessel "BV". When the fluid control valve 26 is actuated to direct pressurized fluid in the direction indicated by arrows "A" into the pressure chamber 70 of the housing 12 and the first clamps 18 are in the unclamped positions, the fluid pressure moves into the cavity 80 in the distal inverted portion 30 of the sleeve 14 in the direction indicated by the arrow "B". When the pressurized fluid enters the cavity 80 in the distal inverted portion 30 of the sleeve 14, the sleeve 14 is forced distally within the lumen "L" of the body vessel "By" and unfurls from about the toroid 62 (or is pulled through the central opening 46 of the housing 12) such that the distal portion 30 of the sleeve 14 extends into the lumen "L" defined by the body cavity "BC" in a substantially linear direction. Although the second clamps 24 are shown unclamped in FIG. 3, it is noted that the second clamps 24 can be clamped such that the sleeve 14 is fed into the lumen "L" of the body cavity "By" on from about the toroid 62.

As illustrated in FIG. 4, the first clamps 18 can be selectively actuated to control the rate at which the sleeve is unfurled from the toroid 62. Similarly, as illustrated in FIG. 5, the second clamp 24 can be actuated to control the rate at which the sleeve 12 is fed through the central opening 46 of the housing 12. The flexibility of the sleeve 14 allows the sleeve 14 to follow the path defined by the body vessel "By" as the sleeve 12 translates through the lumen "L" of the body vessel "By".

The disclosed positioning device 10 is particularly suited for transporting a surgical device, e.g., an endoscope 28, deep within a body vessel "By" during a surgical procedure such as during a colonoscopy. It is envisioned that during such a procedure, the surgical device 40 can be advanced from within the endoscope 28 to treat tissue. For example, the positioning device 10 can be advanced through the lumen "L" of the body vessel "By" to a position adjacent a polyp "P" (FIG. 5) which can be identified with the visualization device 38 of the endoscope 28. When the endoscope 28 is properly positioned within the lumen "L" of the body vessel "By", the surgical device 40 can be actuated to remove the polyp "P". After the surgical procedure is completed, the fluid control valve 26 can be actuated to vent the cavity 80 in the distal portion 30 of the sleeve 14 and the sleeve 14 can be retracted about the toroid 62 to withdraw the endoscope 28 from the lumen of the body vessel "By".

It is also contemplated that the size of the positioning device 10 can be miniaturized to facilitate entry of the sleeve 14 into very small body vessels such as described below in regard to FIG. 6A.

Although not shown, the positioning device 10 need not include a second actuator 20 and second clamps 24. In addition, a support mechanism including a second toroid can be provided on the return side 53 of the housing 12 to provide to wind the sleeve 14 extending from to the return side 53 of the housing 12 such that the sleeve 12 on the return side 53 of the housing 12 can be selectively unfurled by operating the second actuator 20 and second clamps 24.

Figure 6:
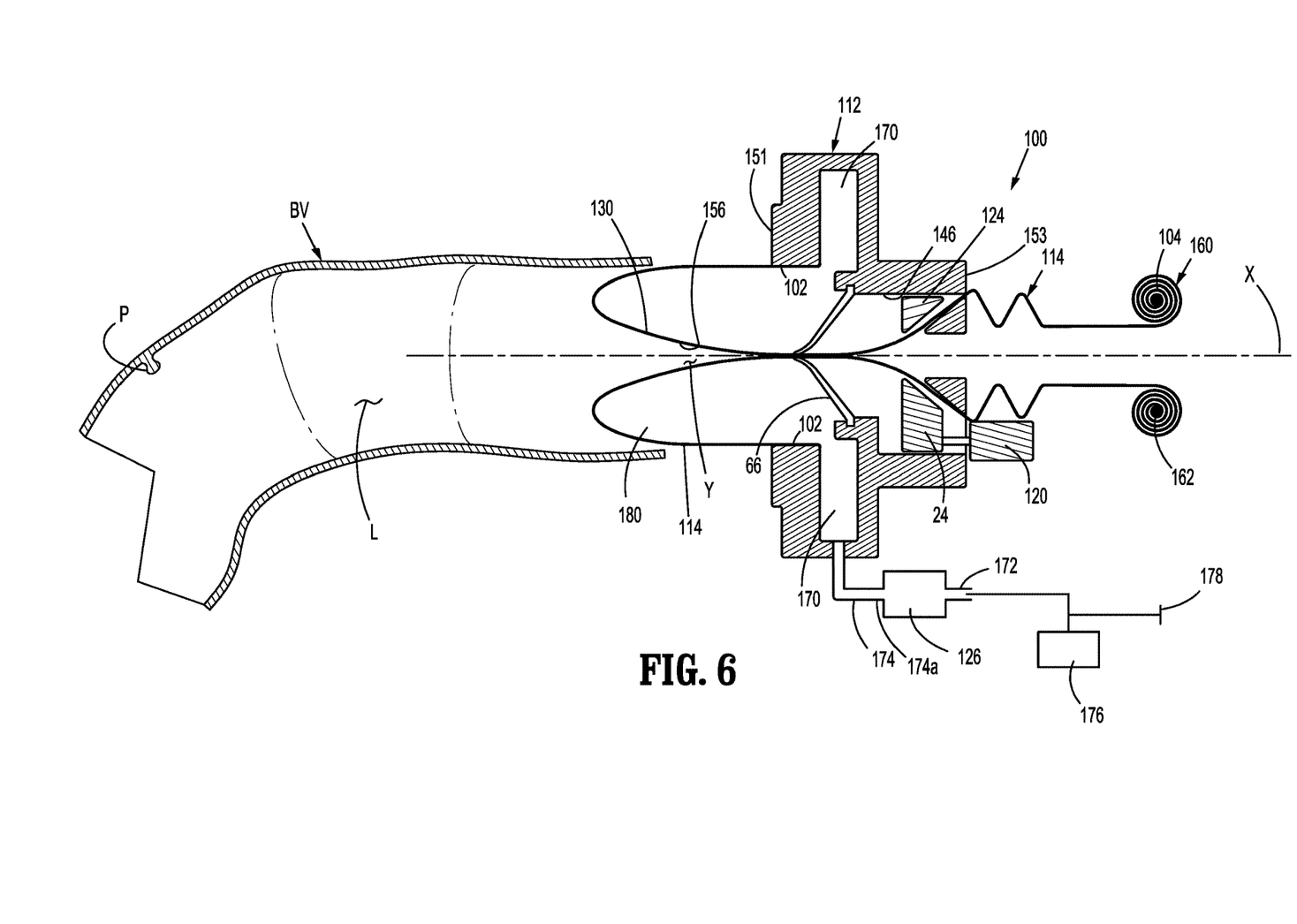
FIG. 6 is a side cross-sectional view of another exemplary embodiment of the disclosed positioning device with the elongate sleeve positioned within an entry opening of a natural body orifice.
Figure 6A:
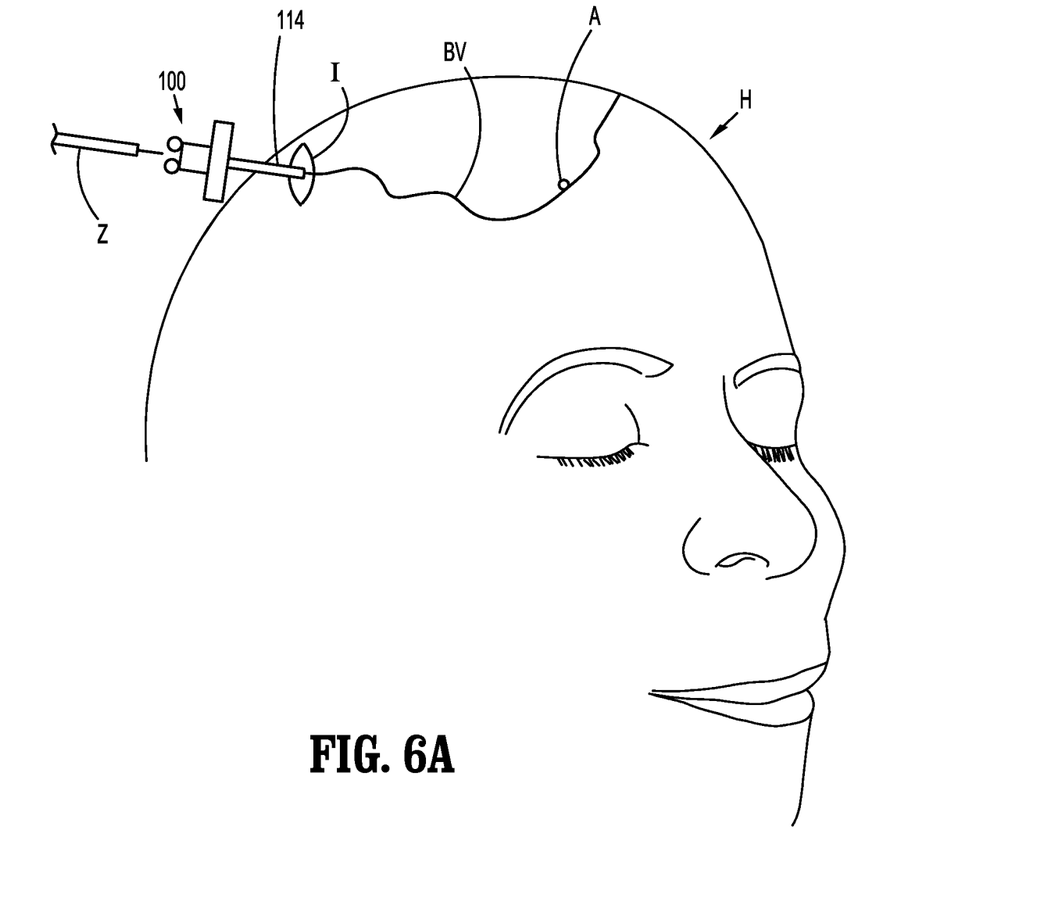
FIG. 6A is a side schematic view of the positioning device shown in FIG. 6 as the sleeve in inserted into vasculature in a brain of a patient.
Figure 6B:
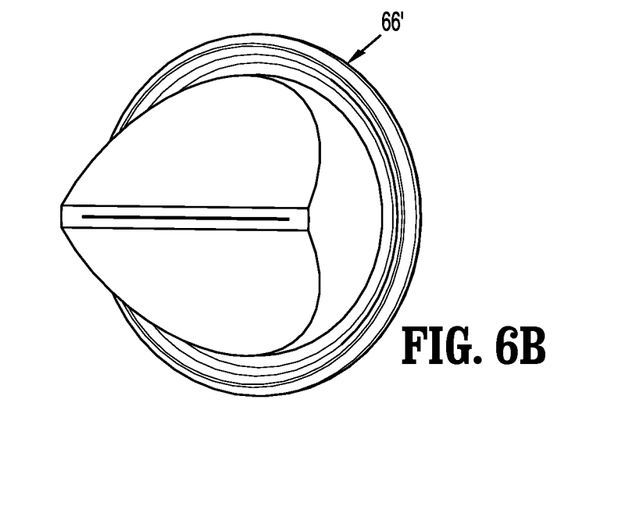
FIG. 6B is a front perspective view of a seal member of the positioning device shown in FIG. 6.
Figure 7:
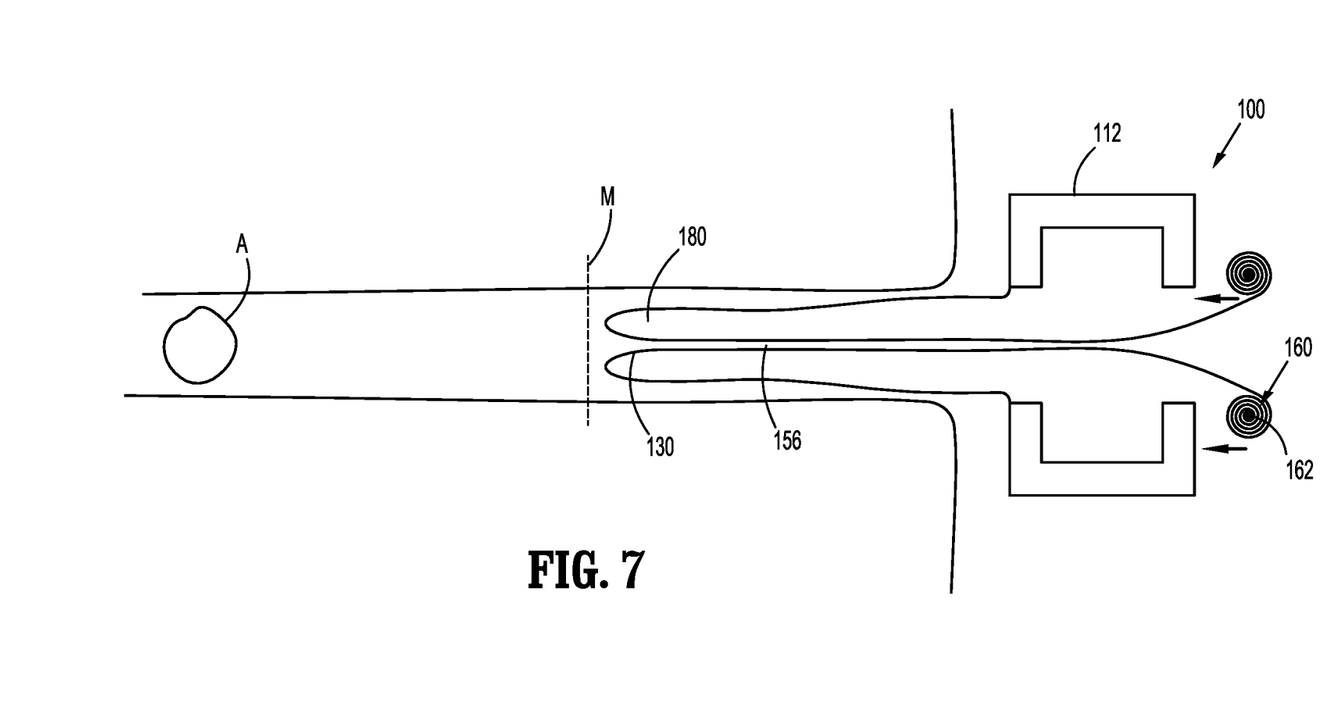
FIG. 7 is a side schematic view of the positioning device with the elongate sleeve positioned through a natural body orifice into a body vessel and extended about halfway to target tissue.

FIG. 6 illustrates an alternate embodiment of the disclosed positioning device shown generally as positioning device 100. The positioning device 100 is substantially similar to the positioning device 10 except that a first end 102 of the sleeve 114 is fixedly secured to the delivery side 151 of the housing 112, the annular sleeve support mechanism 160 including the toroid 162 is supported on the return side 153 of the housing 112 of the positioning device 100 and supports the second end 104 of the sleeve 114, and the first actuator 16 (FIG. 2) and first clamps 18 are eliminated. The housing 112 defines a pressure chamber 170 that communicates with the fluid control valve 126 via a conduit 174. The fluid control valve 126 has an inlet 172 that communicates with a source of pressurized air 176 and an outlet 174a that communicates with the conduit 174. In some embodiments, the inlet 172 may also communicate with a vent 178 that can vent the pressure chamber 170 if necessary.

The positioning device 100 includes an actuator 120 (FIG. 6) which is operable to move the clamps 124 from a first unclamped position to a second clamped position to control delivery of the sleeve 114 from about the toroid 162. The actuator 120 and clamps 124 operate in a manner that is substantially the same as the actuator 20 (FIG. 2) and the second clamps 24 and are not described in further detail herein.

Figure 8:
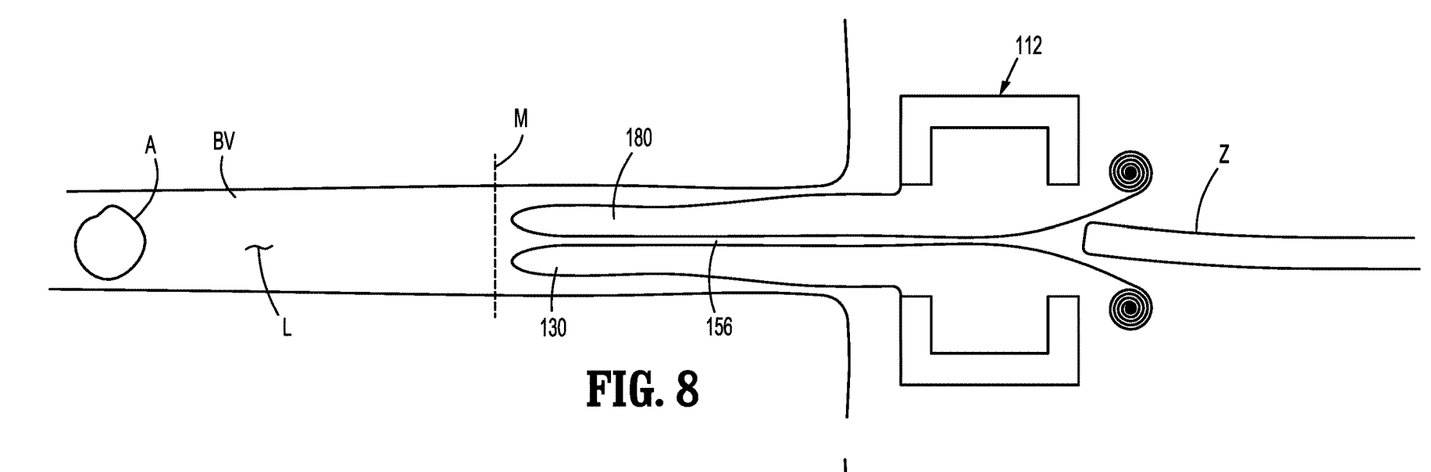
FIG. 8 is a side schematic view of the positioning device shown in FIG. 8 as an endoscope is introduced into a proximal end of the elongate sleeve.
Figure 9:
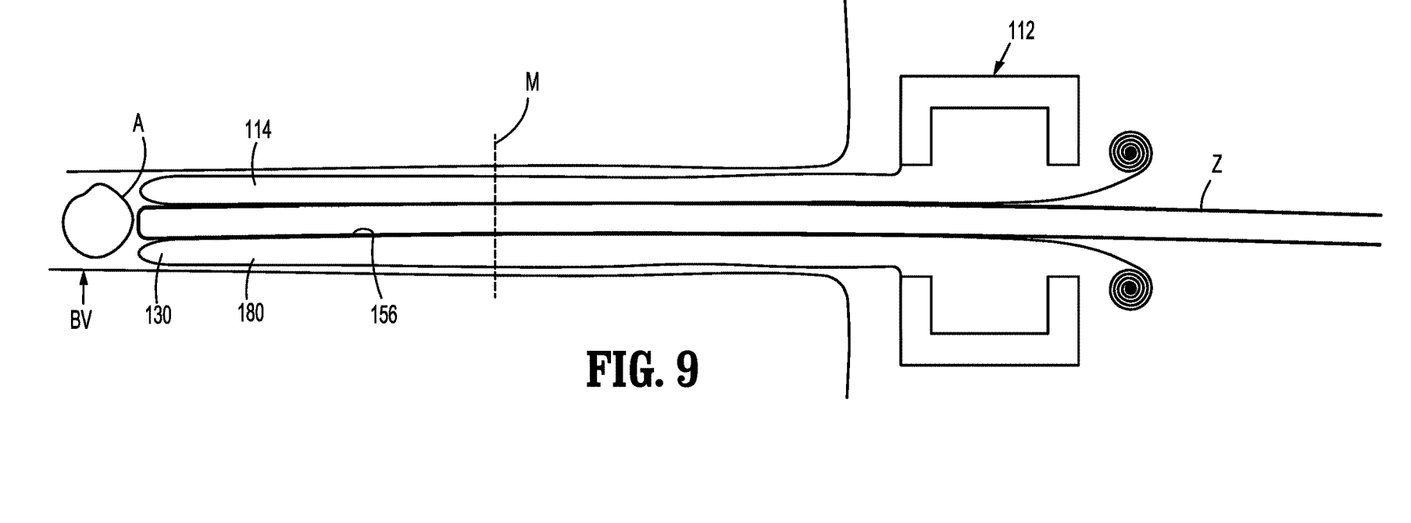
FIG. 9 is a side schematic view of the positioning device shown in FIG. 9 with the endoscope and the elongate sleeve advanced to the target tissue.
Figure 10:
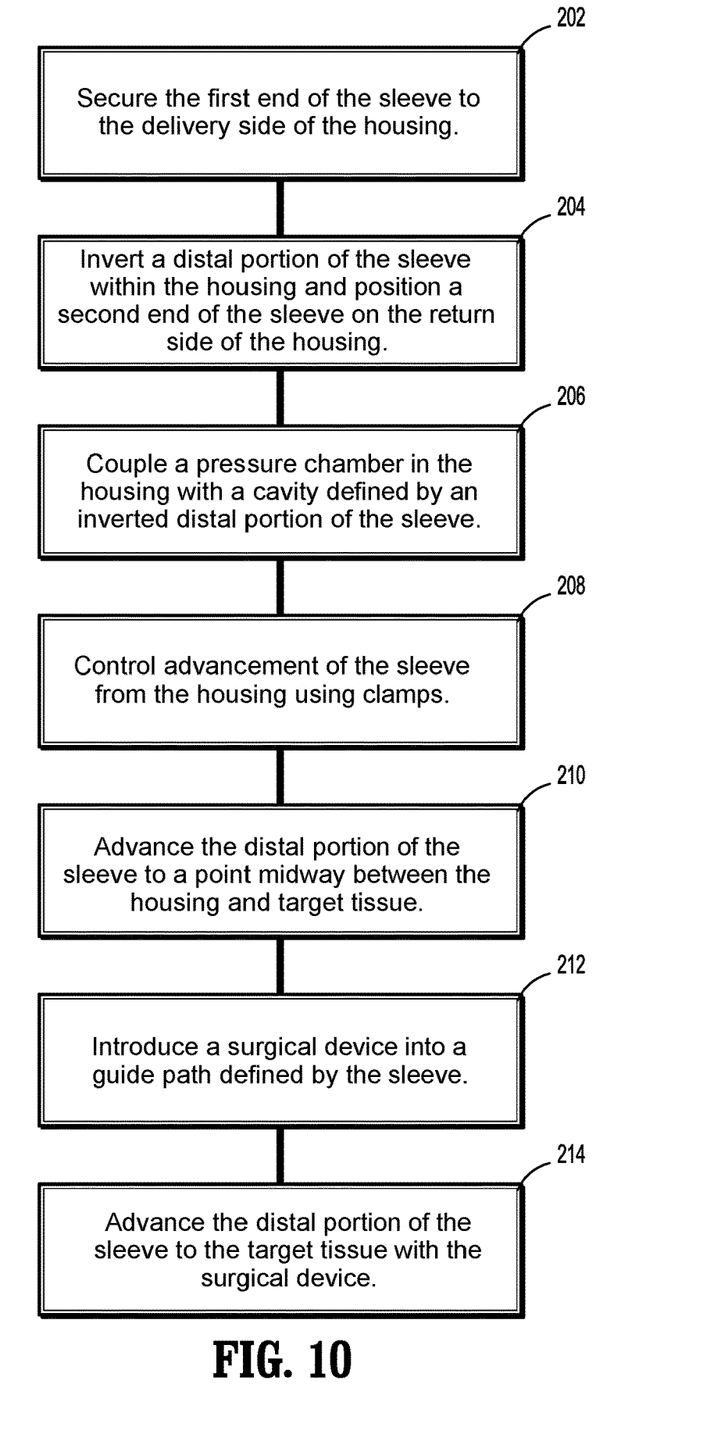
FIG. 10 is a flowchart illustrating one exemplary method for positioning a surgical device adjacent target tissue within a lumen of a body vessel using the positioning device shown in FIG. 6.

In embodiments, the positioning device 100 can be used to provide a pathway 156 to target tissue within a lumen "L" of a body vessel "BV" and is not used to deliver the surgical device "Z" (FIG. 8) to the target tissue "P". As such, the sleeve 114 is advanced to the target tissue "A" independently of the surgical device, e.g., an endoscope. More specifically, the positioning device 100 is used to extend the sleeve 114 through a lumen "L" of a body vessel "By" to provide a guide path 156 through the inverted portion 130 (FIG. 6) of the sleeve 114 to the target tissue "P". The sleeve 114 can be formed of a material that is durable to protect an inner wall of the body vessel "By" during positioning of the surgical device through the guide path 156. After the sleeve 114 is advanced to the target tissue "P", the surgical device "Z" can be pushed through the guide path 156 within the body vessel "By" to access the target tissue "A".

In embodiments, the sleeve 114 is formed of Kevlar or a similar material to protect the inner wall of the body vessel "By" and to guide the surgical device "Z" (FIG. 8) to the target tissue "A". Alternately, the sleeve 114 can be formed of a variety of different materials including, but not limited to, cloth, nylon, polyester, composites or the like. In some embodiments, the sleeve 114 is formed of a woven fabric that includes plastic fibers, e.g., polyethylene, that give the material a fluid tight (air, saline, water) structure. In other embodiments, the sleeve 114 is formed of composite fiber reinforced plastic, where the plastic provides sealing and the fibers provide the material with a high tensile strength.

As discussed above, the sealing member 66' may be in the form of a duckbill valve (FIG. 6B) that is normally closed and seals the guide path 156 until a surgical device "Z" is introduced into the guide path 156. Alternately, other types of sealing members can be used to provide a seal about the inverted portion 130 of the sleeve 114 when a surgical device is not present within the guide path 156.

The sleeve 100 can be formed of a very thin material to facilitate delivery of the sleeve 14 through body lumens having very small diameters. For example, FIG. 6A illustrates the positioning device 100 during delivery of the sleeve 114 into blood vessels in the brain of a patient to treat an aneurysm "A". In such a procedure, the sleeve 114 is introduced into the blood vessel "By" through an incision "I" in the head. The pressure chamber 170 (FIG. 6) is pressurized by opening the fluid control valve 126. As discussed above in regard to positioning device 10, the pressure chamber 170 of positioning device 100 communicates with the cavity 180 (FIG. 6) defined by the sleeve 114 such that the pressure within the cavity 180 forces the distal inverted portion 130 of the sleeve 114 through the blood vessel "BV" to the site of the target tissue "A". After the sleeve 114 is advanced to the site of the target tissue "A", the surgical device "Z" which may include a variety of different tool types can be inserted through the guide channel 156 (FIG. 6) defined by the sleeve 114 to the target tissue "A".

FIGS. 7-10 illustrate an alternate method for delivering a surgical device "Z" to target tissue "A" within a body vessel "By". In this method, illustrated in a flowchart shown in FIG. 10, the first end of the sleeve 114 is secured to a delivery side 151 of the housing 112 (see 202, FIG. 10), a distal portion of the sleeve 114 is inverted within the housing 112 and a second end of the sleeve 114 is positioned on a return side 153 of the housing 112 such that the sleeve 112 defines a central guide channel 156 and the inverted distal portion of the sleeve 114 defines a cavity 180 (see 204, FIG. 10), and the cavity 180 is coupled to a pressure chamber in the housing 112 to facilitate advancement of the inverted distal portion of the sleeve 114 from the housing through a lumen "L" of a body vessel "By" (see 206, FIG. 10).

After the sleeve 114 is coupled to the housing 112, the sleeve 114 is advanced within the body vessel "By". Advancement of the sleeve 114 is controlled with the clamps 124 as described above (208, FIG. 10). In embodiments, the sleeve 114 is advanced in the manner described above to a position "M" about midway to the target tissue "A" (FIG. 7) (210, FIG. 10). After the distal portion 130 of the sleeve 114 is positioned within the body vessel "By" about midway to the target tissue "A", the surgical device "Z" is introduced into the sleeve 114 from the return side 153 of the housing 112 such that the surgical device "Z" is frictionally retained in the guide path 156 by engagement with the sleeve 114 (FIG. 8) (212, FIG. 10). Once the surgical device "Z" is supported within the sleeve 114, the sleeve 114 is advanced to the target tissue to advance the surgical device "Z" to the target tissue "A" FIG. 9) (214, FIG. 10). Since the sleeve 114 is inverted, the surgical device "Z" will be advanced to the target tissue "A" at twice the rate that the distal portion 130 of the sleeve 114 advances to the surgical device "Z". As such, the surgical device Z will reach the target tissue "A" at about the same time that the distal inverted portion 130 of the sleeve 114 reaches the target tissue "A".

Although the disclosure is directed to a positioning device 10, 100 for positioning and/or delivering an endoscope, to a location within a lumen of a body vessel, it is envisioned that the positioning device 10, 100 may be used to position and/or deliver a variety of different types of surgical devices into a lumen of a body vessel including staplers, dissectors, ultrasonic devices, graspers, clip appliers, etc. It is also noted that although the disclosure discloses the use of first and second clamps, it is envisioned that one or more clamps can be provided to selectively control advancement of the positioning device and/or the surgical device within a lumen of a body vessel.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A positioning device for accessing target tissue within a body lumen, the positioning device comprising:
   a housing defining a central bore and a pressure chamber, the housing having a delivery side and a return side;
   a sleeve having a first end and a second end and an inverted distal portion located between the first and second ends, the first end of the sleeve supported on the delivery side of the housing and the second end of the sleeve supported on the return side of the housing, the inverted distal portion defining a cavity and a central guide channel, the cavity in communication with the pressure chamber;
   a source of pressurized fluid communicating with the pressure chamber of the housing;
   an annular support mechanism supported on the housing, wherein the sleeve is wound about the annular support mechanism; and
   a first clamp supported on the housing adjacent the annular support mechanism, the first clamp movable from an unclamped position to a clamped position to control an advancement rate of the inverted distal portion of the sleeve,
   wherein when pressurized fluid is directed to the pressure chamber, the pressurized fluid is directed into the cavity of the inverted distal portion of the sleeve to advance the inverted distal portion of the sleeve away from the housing.

2. The positioning device of claim 1, wherein the annular support mechanism is supported on the delivery side of the housing.

3. The positioning device of claim 1, wherein the annular support mechanism is supported on the return side of the housing.

4. The positioning device of claim 1, wherein the annular support mechanism includes a rotatable toroid.

5. The positioning device of claim 1, wherein the annular support mechanism includes a motor driven toroid.

6. The positioning device of claim 1, further including a first actuator coupled to the first clamp, the first actuator actuatable to selectively move the first clamp between the unclamped position and the clamped position.

7. The positioning device of claim 1, further including a first flexible sealing member positioned about the central bore of the housing, the first flexible sealing member being positioned to engage the sleeve to prevent fluid from passing between the flexible sealing member and the sleeve.

8. The positioning device of claim 7, further including a second flexible sealing member positioned on the housing, the second flexible sealing member being positioned to engage an inner surface of an outer portion of the sleeve to prevent fluid from passing between the sleeve and the housing.

9. The positioning device of claim 8, wherein the first and second flexible sealing members have a tear-drop shaped cross-section.

10. The positioning device of claim 1, further including a fluid control valve including an inlet that communicates with the source of pressurized fluid and an outlet that communicates with the pressure chamber in the housing.

11. The positioning device of claim 10, wherein the inlet to the fluid control valve also communicates with a vent.

12. The positioning device of claim 1, further including a surgical device having a flange, the surgical device supported within the guide channel, the flange positioned distal of the inverted distal portion of the sleeve such that advancement of the sleeve away from the housing moves the surgical device away from the housing.

13. The positioning device of claim 1, wherein the guide channel on the return side of the housing is open to receive a surgical device.

14. The positioning device of claim 1, wherein the sleeve is formed of a material selected from the group consisting of aromatic polyamides, cloth, nylon, polyester, polyethylene, woven fabrics, composites, or the like.

15. A delivery device for positioning a surgical device adjacent target tissue within a body lumen, the delivery device comprising:
   a housing defining a central bore and a pressure chamber that communicates with the central bore, the housing having a delivery side and a return side;
   a sleeve having a first end and a second end and an inverted distal portion located between the first and second ends, the first end of the sleeve supported on the delivery side of the housing and second end of the sleeve supported on the return side of the housing, the inverted distal portion defining a cavity and a central guide channel, the cavity in communication with the pressure chamber;
   a source of pressurized fluid communicating with the pressure chamber of the housing; and
   a surgical device extending through the guide channel, the surgical device including a body having a flange that is positioned distally of the inverted distal portion of the sleeve; and
   an annular support mechanism and a first clamp, the annular support mechanism having a rotatable toroid supported on the housing, the sleeve wound about the rotatable toroid, the first clamp supported on the housing adjacent the annular support mechanism, the first clamp movable from an unclamped position to a clamped position to control an advancement rate of the inverted distal portion of the sleeve,
   wherein when pressurized fluid is directed to the pressure chamber, the pressurized fluid is directed into the cavity of the inverted distal portion of the sleeve to advance the inverted distal portion of the sleeve and the surgical device away from the housing.

16. The delivery device of claim 15, wherein the surgical device is an endoscope.

\* \* \* \* \*